(12) United States Patent
Bjerke et al.

(10) Patent No.: US 10,564,133 B2
(45) Date of Patent: Feb. 18, 2020

(54) DEVICE, METHOD AND SYSTEM FOR AN ULTRASONIC SIGNAL TRANSDUCER ARRAY ARRANGED IN A WHEEL FOR MONITORING THE CONDITION OF AN ARTICLE

(71) Applicant: Elop AS, Moelv (NO)

(72) Inventors: Werner Bjerke, Hamar (NO); Frank Melandsø, Kvaløysletta (NO); Terje Melandsø, Furnes (NO)

(73) Assignee: Elop AS, Moelv (NO)

( * ) Notice: Subject to any disclaimer, the term of this patent is extended or adjusted under 35 U.S.C. 154(b) by 86 days.

(21) Appl. No.: 15/511,600

(22) PCT Filed: Aug. 20, 2015

(86) PCT No.: PCT/NO2015/050140
§ 371 (c)(1),
(2) Date: Mar. 15, 2017

(87) PCT Pub. No.: WO2016/043596
PCT Pub. Date: Mar. 24, 2016

(65) Prior Publication Data
US 2017/0292936 A1    Oct. 12, 2017

(30) Foreign Application Priority Data
Sep. 19, 2014  (NO) .................................. 20141142

(51) Int. Cl.
*G01N 29/04*    (2006.01)
*G01N 29/24*    (2006.01)

(52) U.S. Cl.
CPC ....... *G01N 29/2493* (2013.01); *G01N 29/043* (2013.01); *G01N 2291/0289* (2013.01); *G01N 2291/106* (2013.01)

(58) Field of Classification Search
CPC ............. G01N 29/2493; G01N 29/043; G01N 2291/0289; G01N 2291/106
(Continued)

(56) References Cited

U.S. PATENT DOCUMENTS 3,937,065 A * 2/1976 Milberger ............ G01N 29/045
                                                          73/588
4,098,132 A * 7/1978 Mikesell .............. G01N 29/221
                                                          73/639

(Continued)

FOREIGN PATENT DOCUMENTS

EP           1930722 A2     6/2008
WO    WO-2006067089 A1 *    6/2006    ......... G01N 29/2493

OTHER PUBLICATIONS

Translation WO-2006067089-A1 (Year: 2006).*
Written Opinion of the International Searching Authority issued in corresponding application No. PCT/NO2015/050140, 6 pgs.

*Primary Examiner* — Natalie Huls
*Assistant Examiner* — Monica S Young
(74) *Attorney, Agent, or Firm* — Chamberlain Hrdlicka (57) ABSTRACT

Method, system, and device for ultrasonic signal emission and reception of reflected ultrasonic signal enabling non-destructive analysis of solid material such as in roads, bridges, and other constructions. The device being formed as a wheel (1) where the wheel (1) comprises an array of transducers (20) arranged on a base (3) attached to an axis (2) and a tire section (10) providing a sealed enclosure (7) around the array of transducers (20) where the tire section comprises a plurality of circular protruding sections (12) comprising a tire tread section (11, 22, 24, 25), and a coupling fluid (26) in the sealed enclosure (7) providing an acoustic transparency between the array of transducers and contact points (27) for the tire tread section (11, 24) towards a test material (15).

21 Claims, 10 Drawing Sheets

(58) Field of Classification Search
USPC .......................................................... 73/628
See application file for complete search history.

(56) References Cited

U.S. PATENT DOCUMENTS

| | | | | |
|---|---|---|---|---|
| 4,174,636 | A * | 11/1979 | Pagano | G01N 29/043 73/636 |
| 6,536,553 | B1 * | 3/2003 | Scanlon | G01N 29/069 181/108 |
| 7,472,587 | B1 * | 1/2009 | Loehndorf | G01M 17/02 73/146 |
| 2008/0168833 | A1 * | 7/2008 | Awad | G01M 17/02 73/146 |
| 2011/0013486 | A1 * | 1/2011 | Bond-Thorley | G01N 29/04 367/104 |
| 2013/0047729 | A1 * | 2/2013 | Wigh | G01N 29/043 73/636 |
| 2014/0150557 | A1 * | 6/2014 | De Miguel Giraldo | G01N 29/2493 73/635 |
| 2015/0034222 | A1 * | 2/2015 | Martin | B60C 11/243 152/154.2 |
| 2015/0068312 | A1 * | 3/2015 | Jenkins | G01N 29/262 73/638 |
| 2015/0165238 | A1 * | 6/2015 | Slayton | A61B 18/18 601/2 |
| 2016/0176249 | A1 * | 6/2016 | Brushaber | B60C 23/003 73/146 |
| 2016/0238565 | A1 * | 8/2016 | Gonzalez | G01N 29/2487 |
| 2016/0282314 | A1 * | 9/2016 | Hupkau | G01N 29/043 |
| 2017/0108473 | A1 * | 4/2017 | Bestebreurtje | G01N 29/07 |

* cited by examiner

DEVICE, METHOD AND SYSTEM FOR AN ULTRASONIC SIGNAL TRANSDUCER ARRAY ARRANGED IN A WHEEL FOR MONITORING THE CONDITION OF AN ARTICLE

The present invention relates to ultrasonic signal emission and reception of reflected ultrasonic signal enabling non-destructive analysis of solid material such as in roads, bridges, constructions.

It is a problem to facilitate satisfactory inspection methods and devices for collection of data for imaging of the material itself and of internal constructions, such as reinforcements, and or flaws and faults, for constructions like roads, bridges, or the like.

Solutions have been facilitated for inspection of installations such as pipelines, containers, railway tracks and the like to collect data and to map potential weaknesses and faults. Common for these are that the surface of the material to be inspected is smooth and coupling contact between the installations and the transducers may be comprised by a continuous flow of water between the instruments and the installations, or for example preparation of the installations with coupling gel prior to the execution of the ultrasonic data collection.

Problems arise when large constructions are to be surveyed using ultrasonic signal emission and reception for imaging of the underground, since the available tools are more suitable for random sampling of small areas. If these tools are applied to large constructions the time consumption will be very high if data collection for generation of a complete, or near 100% coverage, analysis of the construction material is required.

Another problem is that instruments for dynamic inspection of material are typically made for inspection of pipes, railroad tracks and the like, where the surfaces of the constructions are smooth and even, and where the surface of the constructions to be tested is easily mapped in that the instruments are guided along the constructions by way of the physical form of the constructions, i.e., along a railroad track, along a pipe etc. Using these types of instruments on concrete or other typical road surfaces and the like will generate large number of faulty measurements due to lack of contact between the instrument and the material under test, e.g. air pockets arises between the instrument and the test surface due to protrusions in the surface, objects and obstacles on the surface or uneven surface, which prohibits the ultrasonic signal to travel into the test material.

There are no known solutions providing ultrasonic data collection for generation of a complete, or near 100% coverage, analysis of the underground using ultrasonic inspection means of large constructions, test material, such as bridges and buildings. Test material can for example be concrete infrastructures with reinforcement bars in buried layers of the concrete, typically at 2-15 cm below the surface of the test material, which are vulnerable to wear and tear, and the state of the concrete and the reinforcements is dictating the capacity of the construction. A weak undetected spot in the concrete may cause the whole construction to collapse with potential harm to people and property. Inspections using measurement techniques with limited capacity are time consuming, and a complete, or near 100% coverage, analysis of construction material are often very expensive, and in many instances they are omitted, resulting in deficient inspections.

Inspection of larger constructions is often performed as visual inspection, and the use of available instruments are used if weak spots are visually detected. Often the method involves taking a core sample from the construction itself, and sending this to a laboratory for further test and evaluation, which is very time and resource demanding. Existing ultrasonic wheel based methods and devices are often based on high frequency signal emission and measuring mechanisms, typically in the multi-MHz range. High frequency signal inspection mechanisms are unsuitable for materials such as concrete and wood.

Existing low frequency signal emission and measuring mechanisms in the lower frequency ultrasound kHz-range, 25 kHz-500 kHz, is limited to stationary test equipment using probes that are arranged at, for example, a suspected weak spot, an then a test sequence of emitting an ultrasonic signal, and receiving and storing/analyzing the received signal for the specific spot is performed. Then, the probe is moved to another spot and the process is repeated. The method is very time consuming, and exclude in all practical sense inspection of large areas with complete, or near 100% coverage.

A problem in underground constructions analysis is to detect vertical cracks in the constructions. Measurement based on reflection only from a vertical crack must, if detected, undergo further detailed testing and time consuming analysis.

The only practical alternative for testing large constructions using available technologies are to use radar based solutions. Systems and devices based on radar technology may cover large areas, but poor resolution represent an unsolved problem for these technologies, and they are not suitable for finding faults or indications of evolving faults that require high resolution imaging for detection. These types of faults may be represented by reinforcements starting to deteriorate, small air pockets or cracks in concrete, areas hidden from radar because of shadow areas behind rocks, reinforcements, sections containing liquid, damp or liquid saturated or other components of the construction.

The present invention provides a device for emission and reception of ultrasonic signal for analysis of large constructions of test material, including test material with uneven surfaces, and ultrasonic data collection. The present invention is suitable for use analyzing at various depths, the depth range also comprising the layer ranging from the surface and up to 15-20 cm into the test material, but not excluding other further buried layers. Depending on the requirements to S/N ratio of received data, frequency of transducer emitted signal and strength, rate of sampling, the depth range of the test material analysis can be varied substantially. The aim is to enable identification of weak spots and faults in the underground of the construction/test material, such as faulty or deteriorated reinforcements in a concrete construction, weak spots due to hidden branches or rotten parts in a wood construction, or other faulty parameters in such constructions or the likes. The present invention provides efficient collection of data using ultrasonic transducer technology, with the ability to utilize low frequency emission in the lower frequency ultrasound kHz range, preferably between 25 kHz and 500 kHz, or more preferably between 75 kHz and 225 kHz, for better performance in test material such as concrete and wood or the like.

The present invention may further be used for emission of ultrasonic signals in higher frequency ranges up to multi MHz range, preferably between 0.5 MHz-10 MHz, or more preferably between 2 MHz and 6 MHz, or even more preferably between 4 MHz and 5 MHz, for ultrasonic data collection from more compact test material, such as steel, carbon fiber, glass fiber or the like.

Although some frequency ranges have been specifically discussed in this document, this shall not limit the present invention, and other frequencies may easily be chosen.

The present invention further provides for a device comprising a wheel comprising ultrasonic transducers for emission and reception of reflected signal, the wheel comprising a plurality of circular sections arranged in the tire tread direction/rolling direction, where each section is aligned perpendicular to one or a group of transducers, and each section comprises a unique tire tread section. In the case an obstacle is met when the wheel is in rolling motion, the influence of the obstacle is mainly affecting the tire tread sections that comes in contact with the obstacle, leaving all the other sections unaffected.

Aspects of the present invention may thus comprise to improve the image resolution resulting from the data collection and analysis, and to improve the S/N ratio in the sampling together with less time consumption for sampling/inspections covering larger areas of constructions/test material, such as bridges, buildings or other constructions by using a dry coupled rolling wheel concept. Examples of other constructions can be, for example, an airplane wing construction, or a gas tanker/ship designed to transport LPG, LNG or liquefied chemical gases in bulk or the like. To achieve this task it is necessary to improve the rate of collecting the data, and further also combine the rate of collecting data with mechanisms that improve the S/N ration in the measurements, and optionally to provide features for absolute positioning or relative positioning or both and include this information in the collected data.

The present invention is optimized for improving efficiency in ultrasonic signal emission and ultrasonic data collection for analysis of materials, even when surfaces of the materials are not even, i.e. because of wear and tear or by the way of construction.

The present invention also provides a method and system for quick and reliable survey of a large constructions where it will be unsatisfactory or impossible to manually keep track of what portions of the construction is already covered by collected data/test samples, thus the invention presents a system and method for automatically keeping track of the portions of the construction covered by the testing device, and ensure efficient coverage of data collection from all portions of the construction/test material in a cost and time efficient manner.

The invention is further defined by the attached independent claims, and further embodiments of the invention are defined by the attached associated dependent claims.

Test material shall in this document be understood to comprise any solid material, such as a mineral, metal or polymer, or composites of these. This includes but is not limited to concrete, ceramics, iron, steel, aluminum, wood, carbon fiber, glass fiber, etc.

Ultrasonic signal emission shall in this document be understood to comprise the emission of any acoustic wave, including pulses, travelling by means of oscillations, including compression and decompression, of the medium in which it propagates. For a solid medium the acoustic wave may take on different modes including, but not limited to, longitudinal pressure wave, transversal shear wave, surface (Rayleigh) wave and others.

Ultrasonic data collection shall in this document be understood to comprise the detection and processing of reflections or transmissions of the aforementioned emitted ultrasonic signals. Different properties of the signals may be collected and analyzed including, but not limited to, amplitude, propagation time, phase and frequency content.

GPS shall in this document mean Global Positioning System.

Absolute position shall in this document be understood to comprise geographic position data as defined by a GPS or antenna triangulation or the like.

Relative position data shall in this document be understood to comprise any definition of position relative a fixed predefined position point. The relative position description may comprise distance in up to 3 dimensions and other parameters such as time and volume.

Control logic shall in this document be understood to comprise any instrumentation and computer means, remote and on device or handheld, used for:
 control of the transducers,
 collect, store and transmit the data from the transducers,
 control of position and direction of movement of the systems of the invention,
 actual positioning in a predefined area above section of a test material,
 status communication and display of the above
 processing of collected data and generation of analysis result Along track shall in this document mean the direction of movement of the device of the invention.

Across track shall in this document mean the direction perpendicular to the movement of the device of the invention.

Transducer or transducer array shall in this document mean all type of ultrasonic transducers, also off the shelf or customized transducer modules comprising control logic and other features.

Reinforcements shall in this document be understood to comprise all type of material that is used to enforce a material of a structure, which can be found named in publications as rebar, armoring, reinforcement bar a. o. E.g. While any material with sufficient tensile strength could potentially be used to reinforce concrete (glass and basalt fibers are also common), steel and concrete have similar coefficients of thermal expansion: a concrete structural member reinforced with steel will experience minimal stress as a result of differential expansions of the two interconnected materials caused by temperature changes.

Membrane and tire tread section shall in this document be understood to comprise the structure of the wheel tire, also the sheer band and the tread, and other constructions/parts of the tire supporting or part of the tread and sheer band.

Coupling fluid shall in this document be understood to comprise any fluid with matching or required transparency properties for the ultrasonic transmission passed through the fluid. Water may be used in many instances.

The invention is further explained in the attached figures that should be interpreted as illustrations of possible embodiments of the invention, but do not represent any limitation of the scope of the invention.

The present invention is a device for ultrasonic signal emission and reception of reflected signal for analysis of test material the device comprising an array of ultrasonic transducers inside a wheel construction with a flexible adaptable segmented tire around the transducer array for providing a rolling motion feature that is also a sealed liquid filled enclosure around the transducer array providing a coupling fluid between the transducers and the tire material that is in rolling contact with the test material.

The present invention further provides a device for ultrasonic signal emission and reception of reflected signal for non-intrusive analysis of a test material. The device comprise more than one array of transducers inside separate wheel constructions with a flexible adaptable segmented tire around the transducer arrays for providing a rolling motion feature that is also a sealed fluid filled enclosure around the transducer arrays providing a coupling media between the transducers and the tire material that is in rolling contact with the test material.

The present invention further provides for a method for ultrasonic signal emission and reception of reflected signal for analysis of a test material, using a device of the invention.

The present invention further provides for a system for ultrasonic signal emission and reception of reflected signal for analysis of a test material, using a device of the invention.

The present invention is exemplified in the figures.

Figure 1:
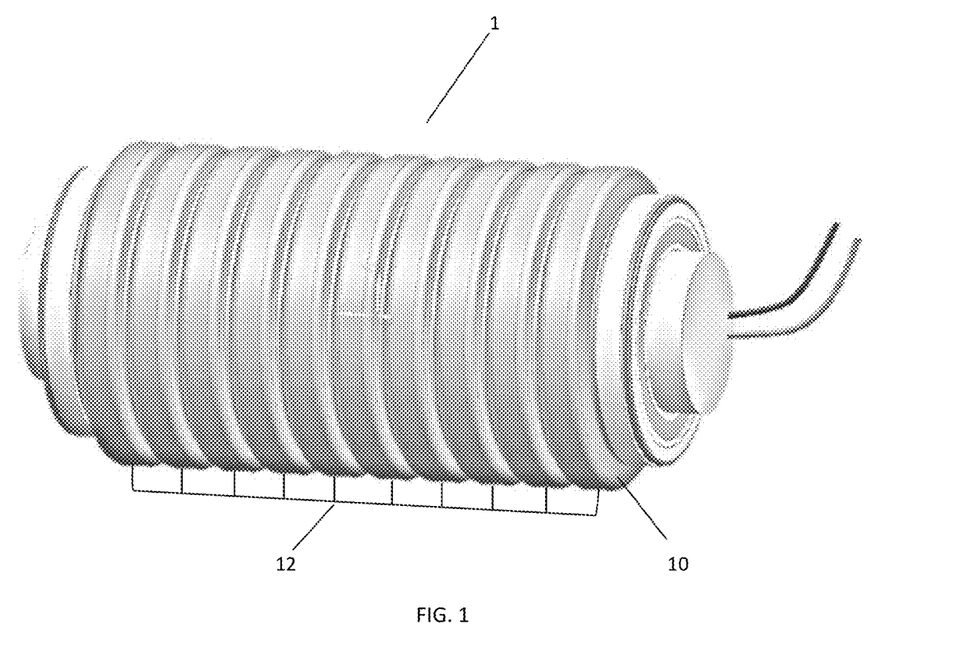
FIG. 1 is a perspective view of a roller unit.
Figure 2A:
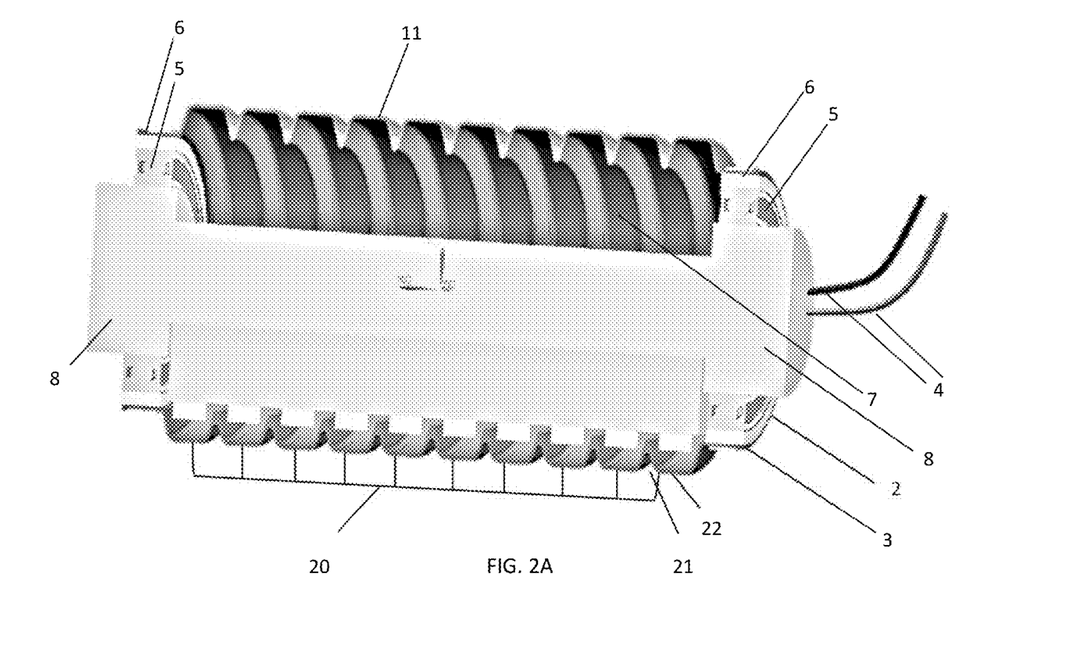
FIG. 2A is a sectional view of the roller cut through a vertical centerline.
Figure 2B:
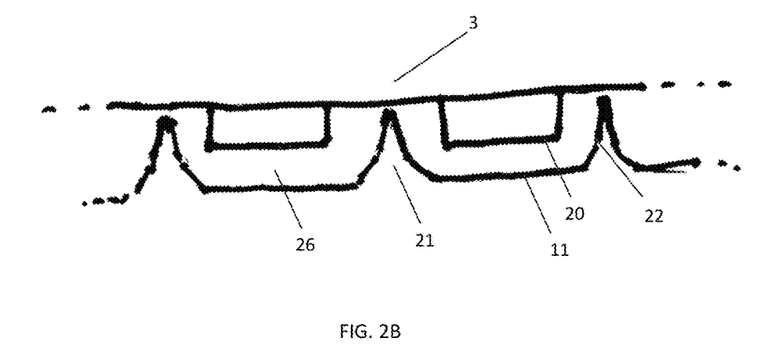
FIG. 2B is a profile detail of an embodiment of sections of the wheel aligned with corresponding transducers.
Figure 2C:
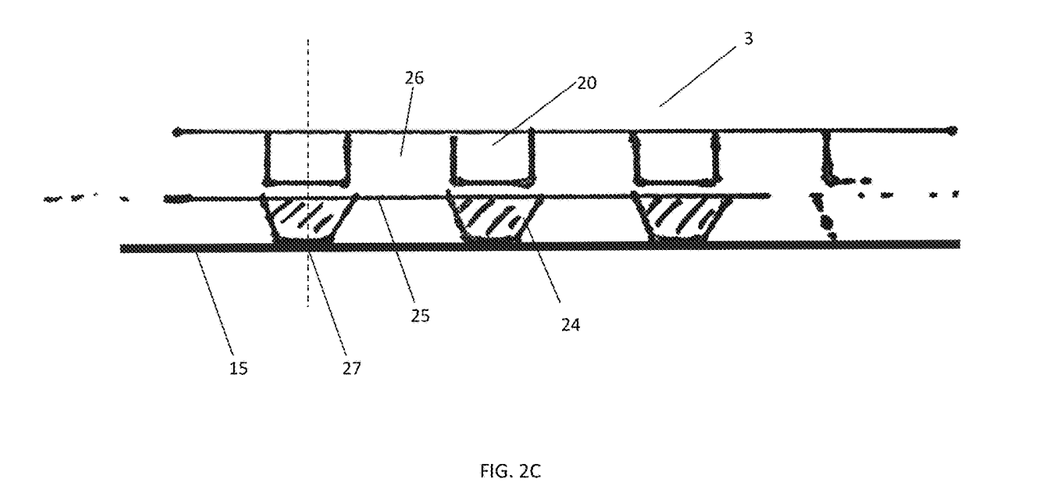
FIG. 2C is a profile detail of an embodiment of sections of the wheel aligned with corresponding transducers.
Figure 3:
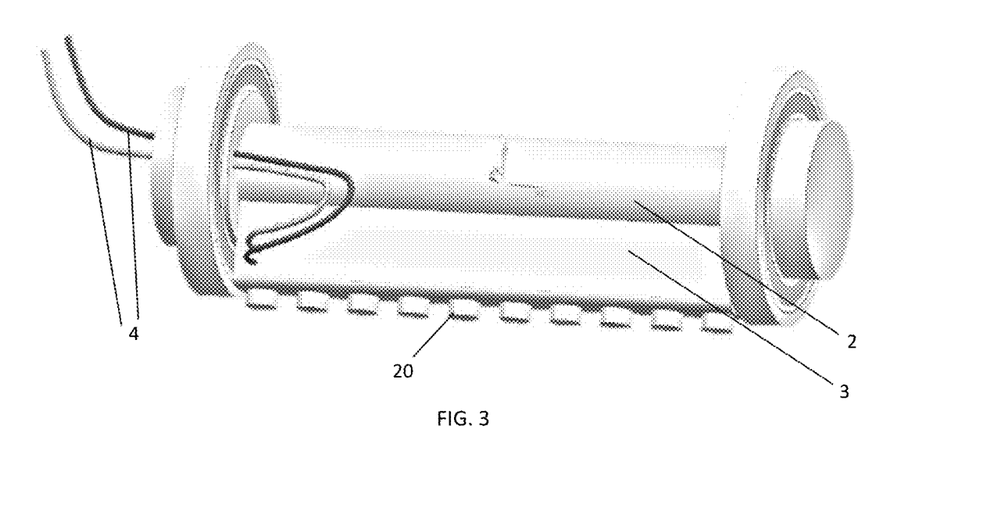
FIG. 3 is a perspective view of the internal of the roller unit.
Figure 4:
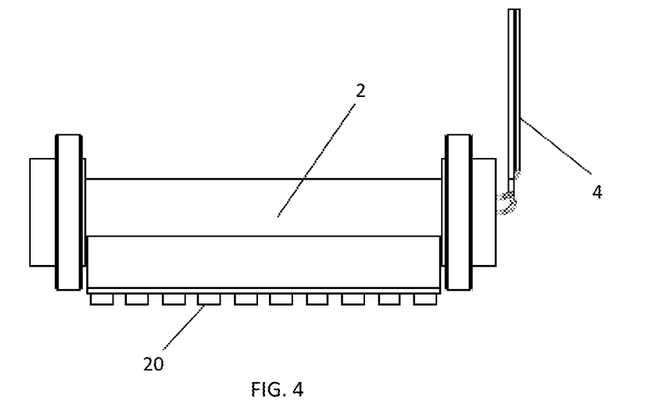
FIG. 4 is a front view of the internal of the roller unit.
Figure 5:
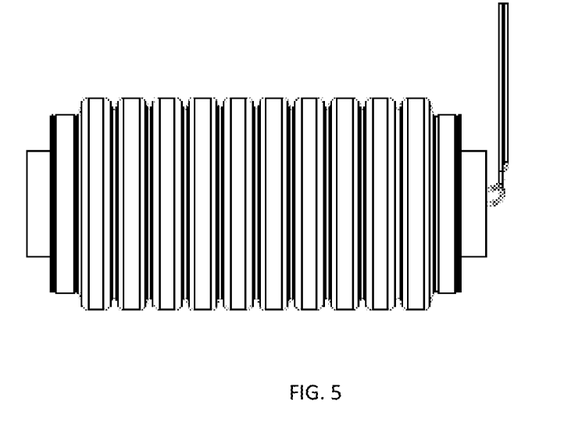
FIG. 5 is a front view of the roller unit.
Figure 6:
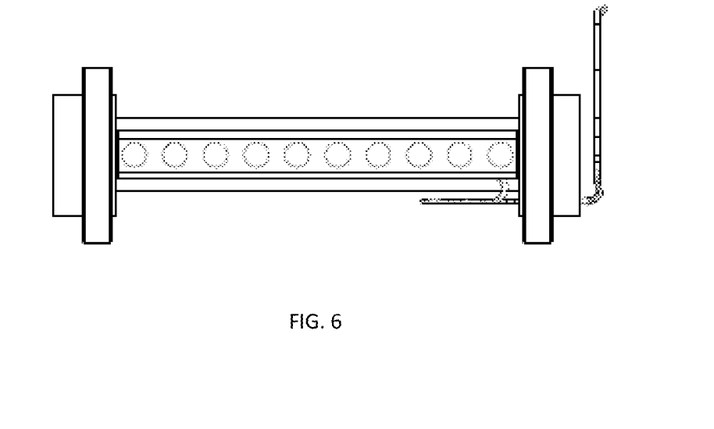
FIG. 6 is a bottom view of the internal of the roller unit.

The wheel construction of the ultrasonic device 1 of one embodiment of the invention provides an enclosure in the form of a tire 10 as shown in FIGS. 1 and 2.

The ultrasonic device comprises an axis 2 providing for a base 3 attached to the axis upon which an array of transducers 20 are arranged.

The transducers 20 are illustrated as cylindrical shaped transducers, but any form of transducer 20 can be used, and shape and size may provide for specific features related to direction of aperture of the signal to be emitted by the transducers 20. Shape may be optimized for specific frequency ranges of the emitted signal.

Size and form of the transducer 20 may also be customized for optimized performance in relation to whether it is to be used only for emitting signal, receiving reflected signal from the test material or both.

The industrialization phase of the invention will be used to find optimum size, form and technology of the transducers 20. The outline of the front may comprise, but not limited by: cylindrical, rectangular, square, elliptic, and other, whilst the shape of the transducer surface (front) may comprise, but not limited by protruding sphere, concave, and convex, single curved or double curved, pyramid or other. Combinations of different forms may be chosen.

Power and signaling cables 4 may be provided for contact between controlling logic (not shown) of the transducers 20 and external means, such as power source, instrument(s), computer(s) and the like. The cables may completely or partly be substituted by wireless communication means or detachable storage media.

The axis 2 provides for peripheral attachment means to bearings 5, such as sealing ball bearings that again provides for attachment bases 6 for a tire/tire section 10. The tire is attached to the tire attachment base in a sealing manner, i.e. with glue, tube clamp, welding or the like.

The tire 10 and the outer part of the bearing 5 will rotate correspondingly to the motion of the device over the test material 15, whilst the axis 2, the transducer base 3 and the transducers 20 will remain in a fixed angular position relative the test material 15 optimized for ultrasonic signal emission and reflected signal reception from the test material 15.

The transducer array position and direction may be set in a number of predefined positions to provide more than one possible angle and/or distance of the ultrasonic transducers relative the material to be tested/inspected. Depending on the wheel material and form, the test material and whether the transducer is used for emitting or receiving or both, the optimal position and angle of the transducer relative the test material will be set. The position and angle may in one embodiment of the invention be changed or alternated between preset positions and angles during operation.

In one use scenario it will be advantageous to be able to ensure that the angle of the emitting signal is vertical in relation to the test material. Additional mechanisms taken from the state of the art technology may be used in combination with the present invention to ensure that the emitting signal is always perpendicular to the surface of the test material or at a predefined angel relative to the surface of the test material.

One such state of the art techniques may be to mount a biased sensor wheel (not shown) that is held in contact with the surface of the test material such that the position of the test material is always known relative to the array of transducers.

In other scenarios there may be desirable to angle the transducers in a defined angle relative the surface of the test material. This may be achieved by similar mechanisms as defined above or other mechanisms.

The various implementations of present invention will provide position data which may be linked to the received signal data. Position data may comprise an absolute position defined by a GPS or other device able to define absolute position, and/or a relative position defined by a starting position defined specifically for the construction to be analyzed, and the by measured/calculated movement from the defined starting point. For example can this be to make the south east corner of the bridge a starting point, and let a tracking ball (not shown) mounted to a carriage of the invention measure any relative movement over the surface from the starting point. Input from the tracking ball and from the known starting point may then be used to define an absolute position of each object described in the resulting analysis constructed of the received ultrasonic reflected data. Instead of a tracking ball, another example would be to use laser and gyro techniques to measure distance to a known reference point and movement. Movement can also be measured by sensing the actual movement of the tires of the invention. Other geographical/relative position definition tools are also encompassed, although not explicitly discussed, in this document.

One potential advantageous aspect of the present invention is to be able to inspect the same test material several times, where each test is performed at different times. E.g. every 5 year, every year, every month, or every day and other intervals. Since the position data is known it is possible to detect changes in exact same location as earlier analysis.

The tire 10 provides for a sealed enclosure 7 around the axis, the transducer array base and the transducer array. The enclosure is filled partly or completely with a coupling fluid 25, such as water. The coupling fluid provides for improved signal transmission between the transducer 20 and the tire section 11, 22, 24, 25 that are in contact with the test material 15.

Unparalleled coupling to uneven surfaces is accomplished by using an elastic material for construction of the wheel, where adaptation to the surface topography is partly utilized by the inherent elastic properties of the tire sections 11, 22, 24 itself. Adaptation may also be further enhanced by the shape of the tire sections 11, 22, 24. Shapes may comprise, but are not limited to: cylindrical, rectangular, square, pyramid, conical, protruding and/or encircling sphere or any other form of protrusions, concave, and convex. Each tire section may be designed as a continuous or repeating form of a trapes, rectangular, triangular, and arched or even button/lug base tire may enhance the signal performance of emission and reception. It is preferred to ensure contact between the tire and the test material when emission and reception of signal happens. Combinations of different shapes may be chosen.

The elastic material may be supported by a harder material 25 as illustrated in FIG. 2C. The supporting material may have matching acoustic/transparency properties to the elastic coupling material 24 on its outside, and the coupling fluid 26 on its inside. The supporting material may be, but not limited to, a type of polymer compound, such as a type of plastic.

Another method for coupling to uneven surfaces may be to use a membrane solution as illustrated in FIG. 2B, where adaptation to the surface topography is utilized by the presence of a coupling fluid 26 behind a membrane 11, 22 comprised of a tire tread section 11 and a sheer band 22. The fluid may be pressurized.

The tire tread section 11, 24 in contact with the test material 15 may for both methods of coupling be an elastic material. The tire tread section 11, 24 could be, but not limited to, an elastomer or rubber-like material, such as a type of polyurethane or nitrile rubber, or other synthetic or natural rubbers, or other types or compounds of polymer material with elastic properties.

The material used in the tire tread section 11, 24, and support material 25 may vary due to different properties dependent on frequency of the emitted signal, such that the material may be different for use on one test material requiring one frequency range, compared with another test material requiring another frequency range. The tire tread section 11, 24 is formed such that one section 12 of the tire tread section 11, 24 is aligned to contact the test material at a contact point 27 on a straight line between a transducer or a number of adjacent transducers and the test material.

The tire tread section 11, 24 form is optimized in shape and numbers of sections 12 such that air pockets between the tire tread section 11, 24 and the surface of the test material 15 is minimized or eliminated, either by a shape that will squeeze out potentially trapped air, or by thread pattern in the tire tread section.

Poor coupling due to irregularities in the surface of the test material 15 will be minimized due to the segmentation of the sectioning 12 of the wheel, and of the form and elasticity of the tire tread section 11, 24.

In one embodiment the tire tread section 11 of the tire 10 is formed as an array of circular sections 12, each section 12 is aligned such that when the tire 10 rolls on the test material 15, each of the tire tread sections 11 provides a dedicated section of the wheel 1 which at any point in time comprises the natural signal path for the emitted and/or received ultrasonic signal between the transducer and the test material.

Compared to prior art the present invention is much less vulnerable to uneven spots in the surface of the test material, since running over an obstacle, such as a small pebble, will only cause minor loss of sampling data, e.g. $\frac{1}{12}$ of the wheel receives no or weak response signal from the underground. The limitations in the response data is depending on the number of circular sections 12 of the wheel that is affected by the pebble. A prior art instrument would for comparison with the same pebble example get an erroneous sample of the complete, or major part of the test range. The main case for deteriorated signal response in prior art is the existence of air pockets between the instrument membrane and the test surface. The blind spot for such prior art instrument will be large and depend on the size of the pebble. The negative effect of running over an obstacle can be even further reduced in present invention depending on the flexibility of the material of the tire tread sections. If a flexible material is chosen it may be possible to maintain contact with the surface of the test material for all wheel sections if an obstacle is run over.

The wheel 1 is at least partly filled with a coupling fluid 26 to a level that ensures that the array of transducers are completely enveloped in the coupling fluid 26, where the coupling fluid 26 also fills the gap between the membrane 11 of the tire section and corresponding transducer in the natural signal path for the emitted and/or received ultrasonic signal between the transducer and the test material.

Figure 7:
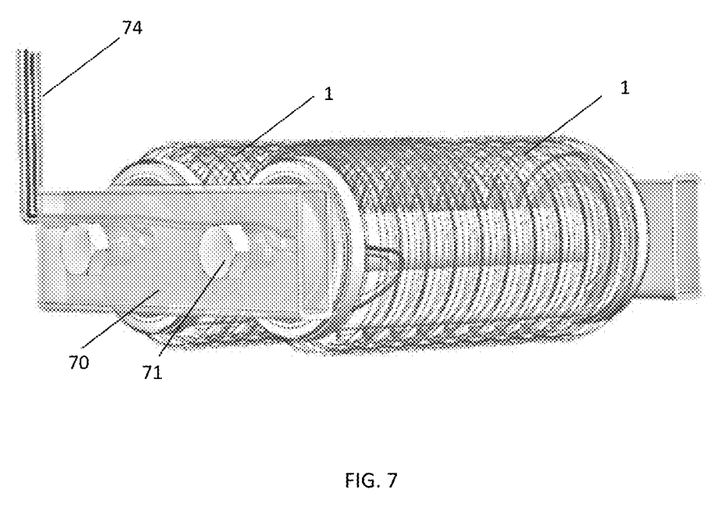
FIG. 7 is a perspective view of a two roller unit with a partly transparent wheel tire section.
Figure 8:
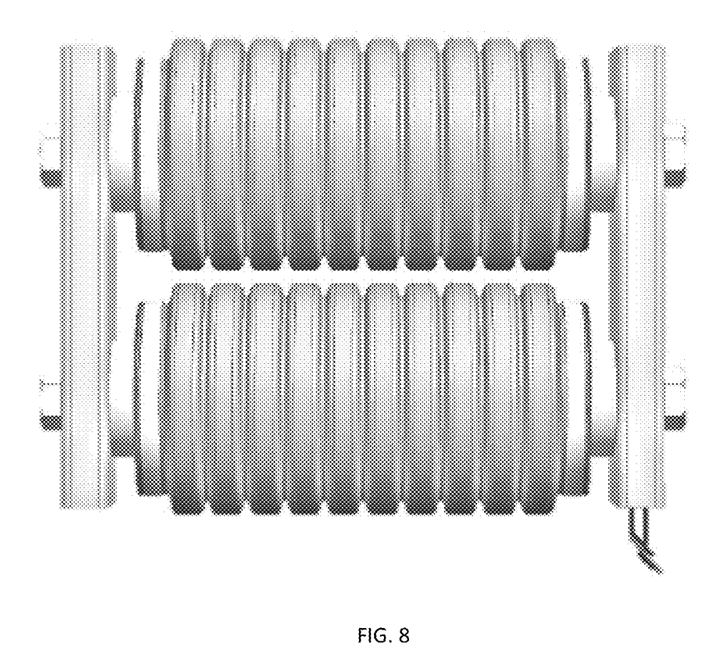
FIG. 8 is a top view of a two roller unit.
Figure 9:
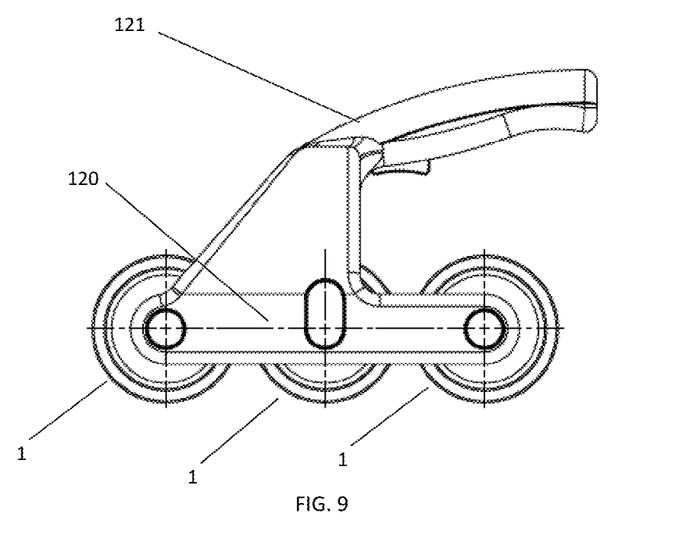
FIG. 9 is a side view of a handheld three roller unit.
Figure 10:
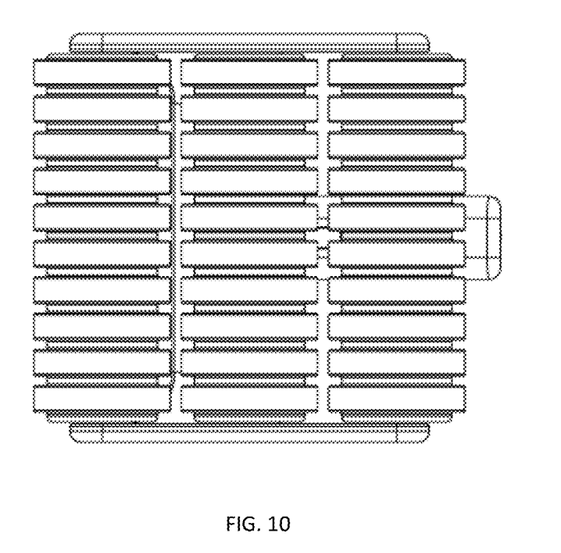
FIG. 10 is a bottom view of a handheld three roller unit.
Figure 11:
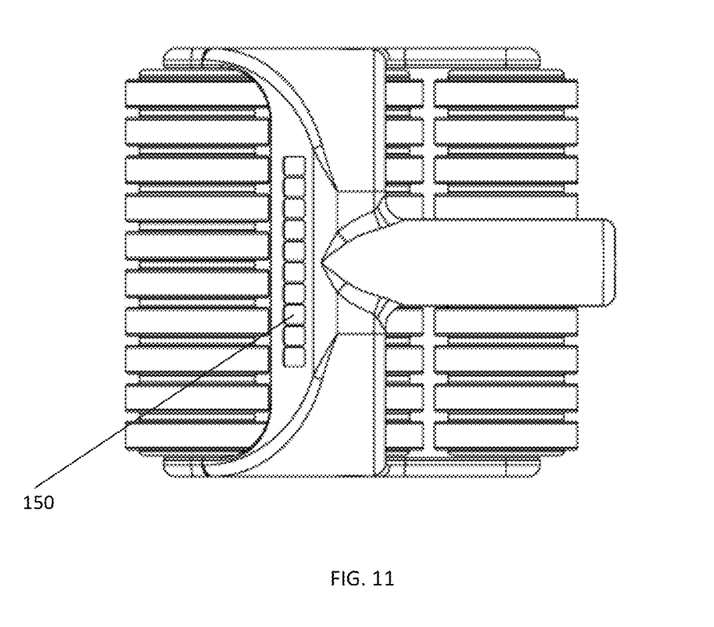
FIG. 11 is a top view of a handheld three roller unit.
Figure 12:
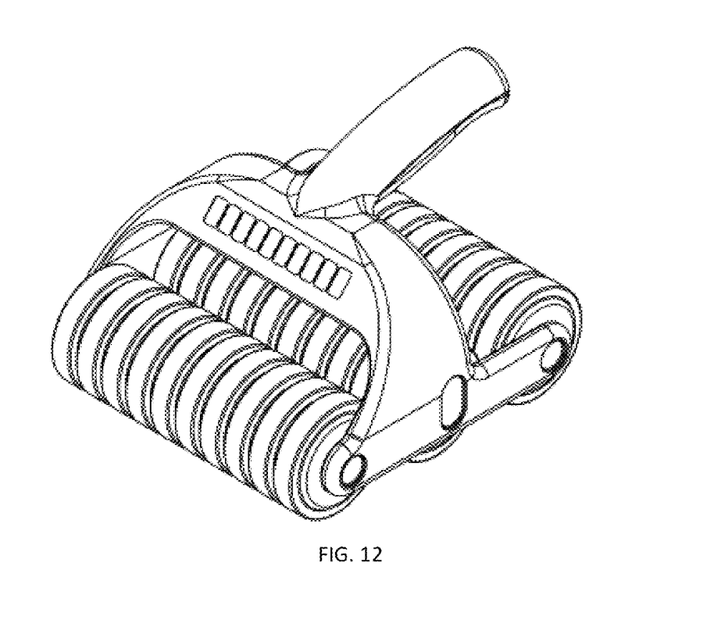
FIG. 12 is a perspective top front view of a handheld three roller unit.

The ultrasonic device 1 of the invention described above may be mounted in a frame 70 as shown in FIG. 7-8. The figures show how two wheels of the invention is mounted in brackets/frame 70 by mounting means 71. The signaling cables 74 are lead through the frame 70.

Another embodiment of the invention is illustrated in FIG. 9-12 showing three wheels of the innovation mounted in a handheld frame 120, where a handle 121 is mounted to the frame 120. The handheld device of the invention may be operated to store received signals together with positional information calculated out from a predefined starting pint by registering the movement over the test material by the rolling motion of the wheels of the invention or other mechanisms such as for example a computer mouse device (not show) or infrared measuring means or the like (not shown).

The handheld device may have on board or attachable, via cable, induction or wireless communication access to: energy source, memory, control logic, input and output control ports, display and audio.

Indication lights 150 may be arranged on the frame for purposes such as indicating contact status between the device and the test material, alarm status if preset signal pattern is received, or if received signal in a specific position is not valid.

Indication lights may be color-coded, such as for example red light if no contact or green light when contact is detected between the device and test material. Other colors and switching pattern may be use for different purposes. One such purpose may be as a self-test indicator to be run prior to each job. It is also possible to use lights in a calibration routine where for example the device may be rolled over a known test material with a known surface with a known expected test result when transducers emit signals in line with a preset test pattern and frequencies. If expected received signal is verified the device is cleared for operation. Verified device may be identified by a preset light pattern displayed by the indication lights 150.

A connected computer may also be used for purposes of storing, calibration, test and evaluation of test results. Computer may be connected by cable, wireless communication or by transfer of data via a storage memory device. A storage memory device may be detachably mounted to the electronic circuits in the device, or may be connectable via an interface at the time of transfer operation.

Figure 13:
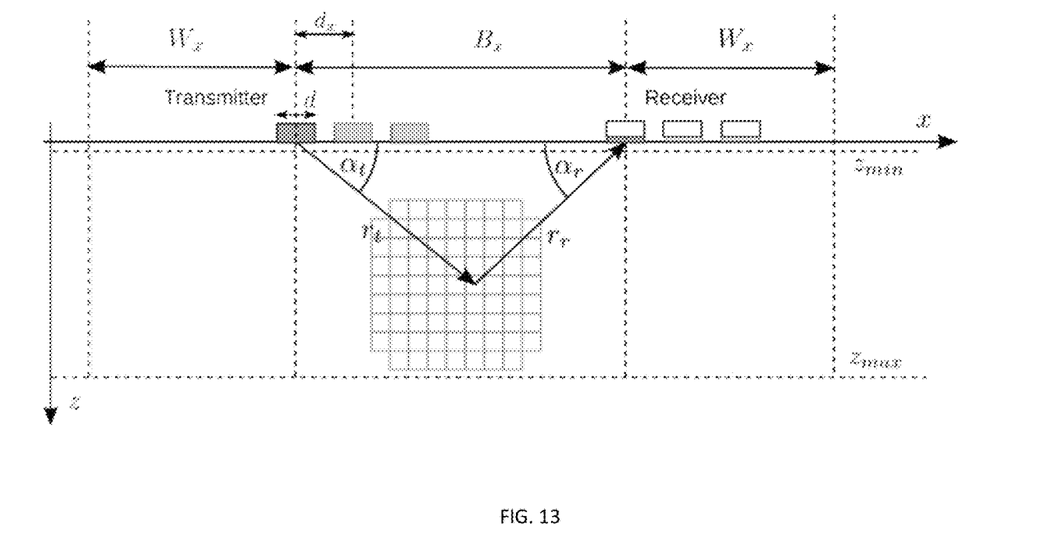
FIG. 13 is a diagram showing along-track geometry example of emitting and receiving arrays of transducers
Figure 14:
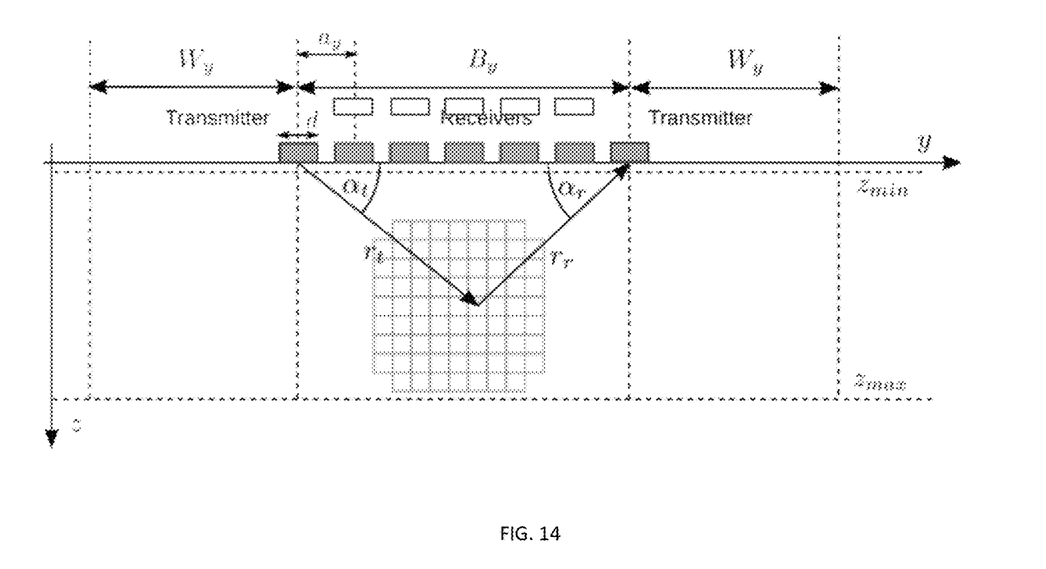
FIG. 14 is a diagram showing cross-track geometry example of emitting and receiving transducers.

The array of transducers may be used in different modes. Two different modes are shown in FIGS. 13 and 14. Other modes can be utilized.

In FIG. 13, it is shown a mode for along-track inspection. One array of transducers, e.g. the trailing wheel of the invention, are used for emitting signals into the underground of the test material, and one array of transducers, e.g. the leading wheel of the invention is used as receiving means for receiving the emitted signals that has traveled into and through the test material and reflected from this.

In FIG. 14, it is shown a mode for cross-track inspection. This is achieved by allocating a number of transducers in one array of transducers for emitting the ultrasonic signal, and a number of transducers of the same array of transducers to receive the signal when reflected from the test material. One transducer may both emit and receive. In one scenario a transducer in the peripheral section of the array of transducers is emitting signals into the underground of the test material and one or more transducers in the mid-section of the array of transducers receives the reflected signals.

It is possible to use more than one array of transducers for receiving, i.e. for the handheld device described above: A transducer in the trailing array of transducers may emit, whilst the two leading arrays of transducers receive, or even all arrays of transducers may be set up to be receiving arrays of transducers were one or more arrays of transducers also emit.

One likely configuration in a system comprising 3 arrays of transducers/wheels such as in the handheld example above is to use the transducers in the middle array of transducers for emission of ultrasonic signals, and the two outer arrays of transducers/wheels for receiving the reflected signal from the test material.

It is also possible to use a single ultrasonic device 1 of the invention, utilizing the cross-track geometry described above.

Transducers may be used for emission or reception only, and both emission and reception, of ultrasonic signals and reflections. A transducer serving as both emitting and receiving transducer for the same ultrasonic signal, i.e. the transducer emit an ultrasonic signal and then wait for the reflections of the signal and then receive the reflected signal, will only receive and detect reflections from objects or the like or material in the path of the emitted signal. If the object is a small vertical crack below the transducer, the reflected signal may be very weak and difficult to detect. In the present invention will a set of transducers, where each transducer either emit or receive an ultrasonic signal, not only measure reflected signals, but also measure the signal transmitted through the test material, and thus be able to measure the lack of reflection, or for example the time-of-flight diffraction. These types of measurements will provide for better S/N ratio in the measurement data. Such configuration will be able to detect the omission of a reflected signal. For example if the signal is obstructed by an air pocket in the test material, and thus the signal propagation is severely obstructed, the receiving transducer will detect that the signal is not received as expected, and a conclusion may then indicate that there is a blocking medium between the emitting and receiving transducer, such as a crack, hole, non-relaying medium or other.

The above additional ability to detect omission of a reflection may be utilized by a single wheel transducer setup of the invention as explained for FIG. 14 above. Enhancing the analyzing effect further may be achieved with the present invention by combining the feature explained in FIG. 14 with the features of using more than one array of transducers (wheels) as, one example of which is explained for the transducer setup in FIG. 13 above. In relation to cracks, obstructions and air pockets, the different transducer setups may be optimized further to detect along track oriented cracks, air pockets, obstructions, with the cross track inspection feature as explained for FIG. 14 above, or across track oriented cracks, air pockets, obstructions, with the along track inspection feature as explained for FIG. 13.

In one embodiment of the invention, the invention may be used to find delamination/air pockets in sandwich structures, such as used in ships or wings (planes, wind turbines). Such sandwich structures may be constructed of multiple layers of different materials. All with potentially different response features relative ultrasonic signals of specific frequencies. The present invention may be controlled in a manner to optimize the response at the specific depth of the test material where a specific sandwich layer interface is located. One could for example examine the interface between the innermost glass fiber layer and the core material in a 3 layer construction comprising an inner glass fiber layer, an outer glass fiber layer and a core polystyrene layer. Other materials and other number of layers may be used.

Another example of embodiment is to use the invention to detect detachments/air pockets under building tiles, such as in a bathroom floor, where the outer layer is ceramic, and the inner layer is of concrete or wood, possibly with a water tight membrane structure in between.

Figure 17:
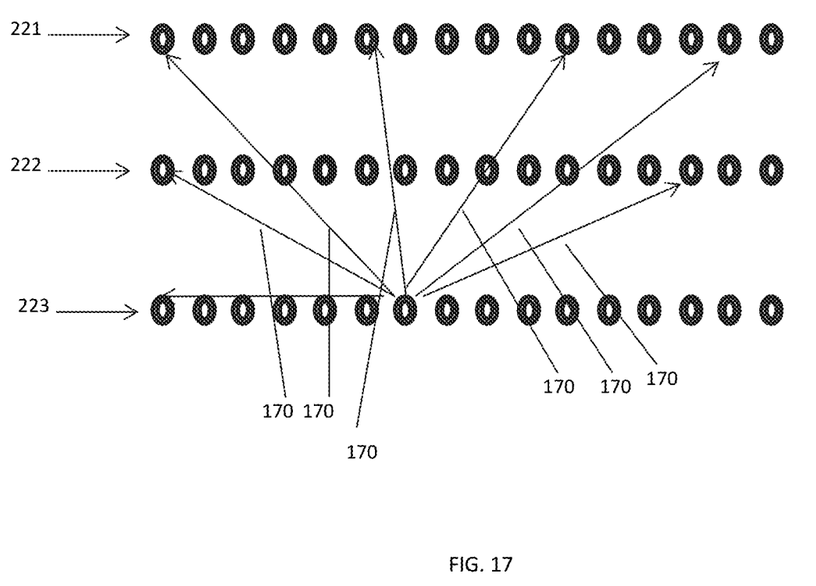
FIG. 17 is a diagram showing an example geometry of an emitting transducer and receiving arrays of transducers.

It is also possible to maximize detection capability by executing a regime of emission and reception of reflected signal where a more complex pattern of shifting the feature of each individual transducer dynamically as the ultrasonic data collection is performed. One pattern would be to let each transducer in turn act as the sole emitting source of a ultrasonic signal, and let all transducer of all wheels (if more than one) be receiving the emitted signal. This way it is possible to map the underground in many directions from perpendicular the motion direction to both sides of the emitting transducer. One example outlining one emitting transducer and 7 receiving transducers indicated by arrows 170 is indicated in FIG. 17. Here three arrays 221, 222, 223 (wheels) of transducers are used. All other combinations may be used from 1 emitting and 1 to 48 (48 is not a limitation but the number used in the FIG. 17) receiving. Other transducer combinations may be used.

The ultimate pattern is to let all transducers in turn be the emitting transducer, and let all transducers act as receivers for all the reflections of an emitted signal. This way it is possible to map all test material from all angles, sideways, forwards, backwards, angled in all directions and directly below. Using the motion of the device of the invention as another parameter it is possible to make several such measurements when moving over the test material. For example an air pocket in the concrete would then be thoroughly exploited from many directions several times, and no "hidden" weaknesses will be omitted.

There are no limits to the size of the arrays of transducers or the wheels used.

Examples of execution regimes may include, but is not limited to, different beam-forming techniques. One example of an execution regime may be SAFT (Synthetic Aperture Focusing Technique).

The more detection data that is collected, the better S/N ratio will be possible to achieve in the analysis process when data is analyzed.

Analysis of the data received from the test material may provide for the compilation of detailed 2D and/or 3D images of the test material at various depths below the surface of the test material, typically 0-15 cm below the surface of the test material.

Figure 15:
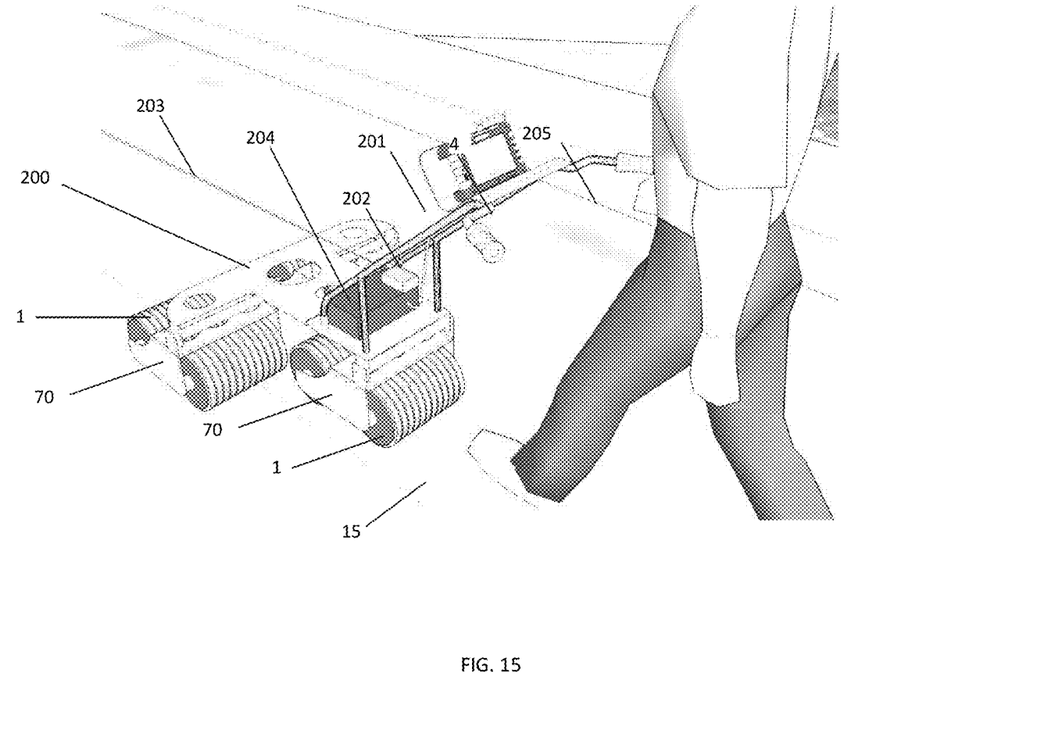
FIG. 15 is a mobile triple two roller carriage system.

FIG. 15 show a system where three pairs of ultrasonic devices 1 of the invention is combined to provide a system for inspection of large volumes of test material. Each pair of wheels is mounded to an individual bracket 70, and the three brackets are mounted to a carriage 200. The carriage further comprises a computing/controlling means 204, a laser measuring device 202, and a display unit 201. Each pair of wheels are individually adapting to the surface, as each section 12 of each wheel is individually adapting to the surface.

The device in FIG. 15, or any variations of a device of the invention, may have on board or attachable, via cable, induction or wireless communication access to: energy source, data storage, control logic, input and output control ports, display and audio.

Indication lights as described for the handheld device above (not shown in FIG. 16) may be comprised in this system as well as in all versions of embodiments of the invention, and for the same purposes as discussed above.

The carriage may comprise means for driving the carriage, e.g. an electromotor (not shown), remote controller features, and further comprise energy source or sources, handles 205 for manually pushing and/or steering the carriage and means for wireless communication with an external control unit (not shown).

Figure 16:
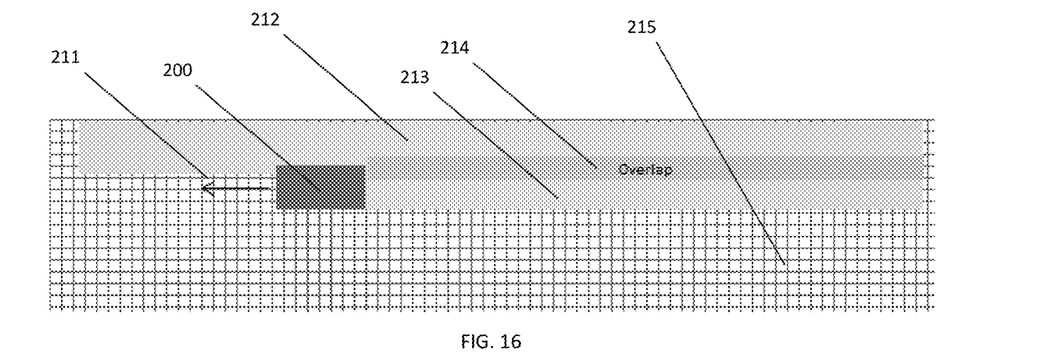
FIG. 16 is an overview of a tracking path scenario for the mobile carriage.

The control unit may be preprogrammed to guide the carriage to cover all segments of the test material as illustrated in FIG. 16. Here a real life representation show the carriage position 200, the direction of movement 211, and the areas that have 212, 213, 214/have not yet 215 been inspected. It may even be possible to distinguish between previous track of inspection 212, current track of inspection 213, and the overlap 214 of current track 213 of inspection relative to the previous 212 track of inspection.

By comparing the received data and the analysis result of this with the corresponding previously performed inspection, it is possible to detect changes in the underground of the test material. For example it may be possible to follow the deterioration of the reinforcement bar in a concrete bridge, and initiate corrective actions at an early stage of deterioration.

The laser unit may be used for measurement of distance in order to define the carriage position on the test material.

Another embodiment example is to use a device of the present invention to sample a painted steel construction. The present invention is able to collect samples of reflected ultrasonic signals that enable the data analysis to uncover cracks and defects in an unparalleled manner without the need to remove paint or other protection layer fixed to the surface of the steel construction.

What is claimed is:

1. A transducer device for emission and reception of ultrasonic signals to analyze a test material comprising a surface sufficiently uneven to form air pockets between the device and the surface, the device being formed as a wheel, comprising:
    an array of transducers arranged on a base attached to an axle of the wheel;
    a tire section comprising a sealed enclosure around the array of transducers and a tire tread section comprising a plurality of circular protruding sections,
    a coupling fluid in the sealed enclosure configured to provide an acoustic transparency between the array of transducers and the contact points for the tire tread section towards a test material, and
    wherein the tire tread section comprises an elastic material configured to conform to the surface to eliminate air pockets between the device and the surface.

2. The transducer device according to claim 1, further comprising:
    bearing means comprising attachment bases and arranged at both peripheral ends of the axle;
    attachment means attached to each bearing means, and
    the tire section attached to the attachment bases so as to provide a rolling capability to the wheel for rolling contact with the test material.

3. The transducer device according to claim 1, wherein each protruding section is aligned to span over one or more transducers, and wherein the tire tread section is in direct contact with the coupling fluid on the inside of the tire tread section facing towards the transducers.

4. The transducer device according to claim 1, wherein the tire tread section comprises a support material comprising a first side providing a contact surface to the coupling fluid, and a second side providing a contact surface to which a coupling material is attached, the coupling material forming the circular sections of the tire.

5. The transducer device according to claim 1, wherein peripheral ends of the axle comprise attachment means for attaching the device to a frame.

6. The transducer device according to claim 1, further comprising electrical cables configured to connect the array of transducers to power.

7. The transducer device according to claim 1, further comprising electrical cables configured to connect the transducers to control logic.

8. The transducer device according to claim 1, wherein the device comprises means for wireless transmission of control data and received signal data.

9. The transducer device according to claim 1, wherein the array of transducers comprises adjustable attachment means to the base or the axle, in order to change the angle and/or distance of the array of transducers in relation to the test material.

10. The transducer device according to claim 1, wherein each individual transducer in each of the arrays of transducers acts as either emitting transducer, or receiving transducer, or both emitting and receiving transducer.

11. A transducer carriage device for ultrasonic signal emission and reception from a test material comprising a surface sufficiently uneven to form air pockets between the device and the surface, the device comprising transducer devices, each transducer device being formed as a wheel, wherein the wheels are attached to a frame, the wheel comprising a plurality of circular protruding sections comprising a tire tread section, wherein the tire tread section comprises an elastic material to conform to the surface to eliminate air pockets between the device and the surface.

12. The system according to claim 11, the system further comprises a display means.

13. The system according to claim 11, the system further comprises a tracking means for providing relative position.

14. The system according to claim 11, wherein the control mechanism for steering the carriage comprises a handle for manual guidance or a remote controlled motor connected to driving means for moving the carriage.

15. The system according to claim 11, the system further comprising a computer means for receiving the received ultrasonic signal data and for processing the data.

16. The system according to claim 15, wherein the computer means comprises a remote computer means.

17. A system for ultrasonic signal emission and reception to analyze a test material comprising a surface sufficiently uneven to form air pockets between the system and the surface, the system comprising:
- one or a plurality of transducer devices, wherein each transducer device is formed as a wheel comprising a plurality of circular protruding sections comprising a tire tread section, wherein the tire tread section comprises an elastic material to conform to the surface to eliminate air pockets between the device and the surface,
- a carriage to which the one or a plurality of transducer devices are mounted,
- a control mechanism for steering the carriage along a path over the surface of a test material, and
- control logic for controlling the carriage, the transducers, and storing and transmission of data received by the transducers.

18. The system according to claim 17, the system further comprises a navigation means for providing absolute position.

19. A method for emitting and receiving of ultrasonic signals to analyze a test material comprising a surface sufficiently uneven to form air pockets between a wheel and the surface, comprising:
- rolling a tire section along the surface, the tire section comprising a sealed enclosure around an array of transducers and a tire tread section comprising a plurality of circular protruding sections;
- conforming the tire tread section to the surface to eliminate air pockets between the tire section and the surface as the tire section is rolled;
- emitting ultrasonic signals from at least one transducer of the array of transducers as the tire section is rolled;
- receiving reflections of the emitted ultrasonic signals from the test material with one or a plurality of transducers of the array of transducers; and
- transferring and storing the received ultrasonic signals to a computer means and analyzing the received ultrasonic signals.

20. The method according to claim 19, the method further comprising:
- moving a carriage along a predefined path;
- emitting ultrasonic signals from individual transducers of the array of transducers according to a predefined emission pattern; and
- receiving the reflected ultrasonic signal from the test material with one or a plurality of transducers of the array of transducers configured to be receiving transducers for the individual emitted ultrasonic signal.

21. The method according to claim 19, the method further comprising:
- comparing the result of the analysis of a section of a test material with a previous analysis of the same section of the test material; and
- identifying changes in the test material.

\* \* \* \* \*